United States Patent [19]
> Imperante et al.

[11] Patent Number: 5,260,055
[45] Date of Patent: Nov. 9, 1993

[54] FATTY CARBOXYLIC SILICONE AMINE SALTS

[75] Inventors: John Imperante, 4 Lance Rd., Somerville, N.J. 08833; Anthony J. O'Lenick, Jr., Lilburn, Ga.

[73] Assignee: John Imperante, Lebanon, N.J.

[21] Appl. No.: 821,044

[22] Filed: Jan. 16, 1992

Related U.S. Application Data

[63] Continuation-in-part of Ser. No. 656,834, Feb. 19, 1991, Pat. No. 5,115,049.

[51] Int. Cl.$^5$ .............................................. A61K 7/075
[52] U.S. Cl. ........................................ 424/71; 424/70
[58] Field of Search ............... 424/70, 69, 47, 401; 514/784; 528/26

[56] References Cited

U.S. PATENT DOCUMENTS

| | | | |
|---|---|---|---|
| 4,559,227 | 12/1985 | Chandra et al. | 424/70 |
| 4,785,067 | 11/1988 | Brumbill | 528/26.5 |
| 4,844,888 | 7/1989 | Zawadzki | 424/69 |
| 4,960,845 | 10/1990 | O'Lenick, Jr. | 528/15 |
| 4,973,643 | 11/1990 | O'Lenick, Jr. | 528/15 |
| 5,073,619 | 12/1991 | O'Lenick, Jr. | 528/26 |
| 5,115,049 | 5/1992 | Imperante et al. | 528/26 |

*Primary Examiner*—Thurman K. Page
*Assistant Examiner*—N. Levy

[57] ABSTRACT

The invention discloses a process of conditioning hair and skin which comprises contacting the skin or hair with an effective conditioning amount of a series of novel fatty carboxylic acid salt of organofunctional silicone amine. The amino pendant functionality is present within the polymer. Compounds of the invention by virtue of their being salts, deposit on the surface of various substrates. Thereby altering the substrate's surface physical properties. The desirable durable properties which can be given to substrates include; softness, lubrication and hydrophobicity. The compounds of the present invention are prepared by the neutralization of a silicone amine with a fatty carboxylic acid.

18 Claims, No Drawings

FATTY CARBOXYLIC SILICONE AMINE SALTS

RELATED APPLICATION

This application is a continuation in part of copending application Ser. No. 07/656,834 filed Feb. 19, 1991, now U.S. Pat. No. 5,115,049.

BACKGROUND OF THE INVENTION

1. Field of Invention

The invention discloses novel fatty carboxylic acid salts of organofunctional silicone useful in the preparation of a variety of personal care formulations. The products are the fatty carboxylic acid salts of silicone polymers which contain amino pendant functionality. Compounds of the invention deposit on the surface of various substrates, like hair and skin. Thereby altering the surface properties. The properties which can be given to substrates include; softness, lubrication and hydrophobicity. The compounds of the present invention function as humectants and protective barriers on the skin. Additionally, they impart a high level of sheen and softness to the skin. The compounds of the present invention can also be used as partial or total substitute for petrolatum. Another surprising aspect of the compounds of the present invention is their lack of irritation and toxicity when applied to eyes and skin. They are alos non comedogenic.

The compounds of the present invention are prepared by the complete neutralization of a silicone amine with a fatty carboxylic acid. The compounds of the present invention, in stark contrast to fatty amine derivatives, show no irritation to skin and no oral toxicity when tested at 5.0 gms/kg body weight.

2. Description of the Arts and Practices

Silicone compounds have been known to be active at the surface of hair and skin. Silicone oils make good lubricants and are very stable to oxidation, however, their high cost and lack of efficiency at low concentrations as well as low durability have made their acceptance in commercial products quite low. In all instances, commercially available quats are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery is to the surface by hydrophobic binding, not chemical bonding. At the surface, the dimethylpolysiloxane is a very effective lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

One major area in which the compounds of the present invention find applications is in so called two in one shampoos. That is shampoo compositions which also condition and soften. Soiled human hair is shampooed to remove sebum that is naturally secreted by the head, as well as soil and other atmospheric contaminants that accumulate on the hair. Sebum accumulates on the hair in a short time, leaving the hair with a greasy, dirty feel and poor manageability. The most effective shampoos for cleansing the hair and for the removal of the atmospheric contaminants and sebum, are those that contain high lather anionic detergents, such as the long chain alkyl sulfates or ethoxylated long chain alkyl sulfates. These anionic detergents are very effective for cleansing the hair but after rinsing with water, leave a the hair in a condition often called "creak". In this condition the hair is likley to become extremely tangled, unmanageable and cosmetically unappealing.

Thoroughly cleansed hair, which is stripped of natural oils, is extremely difficult to comb in either the wet or dry state because the individual hair fibers tend to snarl, kink, and interlock with each other. Particularly prior to complete drying of thoroughly cleansed hair, the hair is very difficult to comb, brush or manage. This is refferred to as poor wet combability. Even after complete drying, the thoroughly cleansed hair remains difficult to comb or brush and does not set well. Additionally, thoroughly clean, dried hair also has undesirable electrostatic properties in a low humidity atmosphere that causes the hair to "fly away", thereby further reducing the combing or brushing property of the hair.

After shampoo hair conditioning compositions have been used for many years. One of the problems with such a conditioner is that they commonly contain large quantities of fatty quaternaries which are irritating to the eyes, build up on the hair and cause other problems with altering the feel and appearance of the hair. Some fatty quaternary compounds are known to be toxic to aquatic organisms. In addition this approach entails an additional step which is time consuming.

An approach toward eliminating the time consuming problem with after shampooing conditioners has been the preparation of a conditioning shampoo. While several products have been on the market, there has been some major difficults encountered. One major problem has been incompatibility of the shampoo composition due in large part to incompatability between anionic surfactants and the fatty cationic compounds which are the conditioning agents commonly used. Contact between an anionic surfactant and a cationic surfactant produces a precipitate that forms immediately and significantly reduces the cleaning and conditioning properties. Another problem has been the reduction in cleansing and conditioning effectiveness. This can occur even when the incompatability problems have been overcome by modification of the formulation. This incompatibility between an anionic surfactant and a cationic conditioning compound is well recognized by those skilled in the art. For example, Sagarin in Cosmetics, Interscience Publishers, Inc., New York, p. 538 (1957), states that anionic and cationic compounds cannot be used in combination because they react to form insoluble salts. As will be shown, the present compositions make use of a complex which not only is soluble, but is conditioning and emulsifying for insoluble silicone. One of the reasons for this being a surprising discovery is that the above mentioned literature references teach away from the present invention. Other novel aspects of the present compositions and processes for their use will become clear by reading the rest of the disclosure.

Another attempt to overcome the incompatibility problem in the formulation of conditioning products is exemplified by the following patents that disclose compositions containing surfactants that are not anionic, specifically nonionics, amphoterics and zwitterionics surfactants can be formulated into a conditioning composition. Examples of this type of product is shown in the following patents; U.S. Pat. No. 3,849,348 to Hewitt; U.S. Pat. No. 3,990,991 to Gerstein; and U.S. Pat. No. 3,822,312 to Sato. Compositions based upon these alternate surfactant types do not have the detergent properties needed for successful shampoos and have enjoyed minimal commercial success.

Another attempt to overcome the instability problem encountered using cationic and anionic surfactants has been to replace the fatty quaternary compound in the composition with a non-fatty water insoluble conditioning agent such as the nonvolatile silicones. This approach has become well recognized in the art as providing a degree of softness to the hair. The formulation of the so called two in one shampoo (also known as shampoo plus conditioner) has been attempted in recent years. Many of these compositions contain highly insoluble silicones and consequently require elaborate formulation additives to thicken and otherwise hold the compositions together. The result is inferior preformance, due in part to lack of homogenity of the compositions. It is not uncommon to see the insoluble silicone floating on the top of a bottle of two in one shampoo. These formulation additives which increase stability, also have a negative effect upon performance of the composition.

Many attempts have bene made over the years to product a truly stable conditioner compostion having a dispersed, insoluble, nonvolatile silicone material suspended therein, while retaining the cleansing and conditioning performance of the conditioning shampoo. This stability problem is particularly prevalent in conditioning products containing an anionic surfactant and a cationic conditioning material which, as outlined above, by themselves tend to interact and present stability problems. A variety of materials have been proposed for inclusion in silicone containing conditioners for purposed of thickening and stabilization, such as xanthan gum, long chain acyl derivatives, long chain amide oxides, and long chain alkanolamides as disclosed in U.S. Pat. Nos. 4,788,006; 4,704,272; and 4,741,855. The effect of incorporating thickening agents and other stabilizers is a greasy unappealing feeling on the hair and a greasy build up on repeated use.

Silicones added to shampoo compositions have been known for many years. Several examples are the following U.S. patents: U.S. Pat. No. 2,826,551 issued Mar. 11, 1958 to Green; U.S. Pat. No. 3,964,500 issued Jun. 22, 1976 to Drakoff; U.S. Pat. No. 4,364,837 issued Dec. 21, 1982 to Pader; British Pat. No. 849,433, issued Sep. 28, 1960 to Woolston; U.S. Pat. No. 4,741,855, to Grote, et al.; U.S. Pat. Nos. 4,788,006 and 4,902,499 to Bolich, Jr. et al. and U.S. Pat. No. 4,704,272 to Oh, et al. The diversity of approach used by the various inventors and the extended time frame over which work has been attempted, demonstrates a long felt, and unfulfilled need for a truly functional conditioning product.

U.S. Pat. No. 5,034,218 issued July 1991 to Duvel teaches that conditioning shampoo compositions can be prepared using non volatile silicone compounds and a variety of surfactants, fatty quaternary compounds, fatty alcohols, and polymeric suspending agents. The need for all these components to make a stable or metastable composition is common in the preparation of conditioning products. This type of formulation is appreciably different from the compositions of the present invention in that the present compositions are conditioners which are anhydrous systems rather than aqueous emulsions or thickened dispersions additionally, the present compositions do not contain many of the fatty materials which aside from building up on hair are known to be irritating to eye and skin.

One approach to overcome the undesirable effects of either post treatment with an insoluble fatty quaternary or fatty alcohol containing conditioners, or the incorporation of silicone into a thick stabilized shampoo is to pre-treat the hair with a water soluble quaternary. U.S. Pat. No. 4,061,150 issued Dec. 6, 1977 to Dasher et al, teaches that dilute aqueous water soluble fatty quaternary compounds can be used to precondition hair before shampooing. This technology, while representing a significant advance over the art practiced before it, did not provide the advantages of silicone products offered by the present invention.

One major problem which is encountered formulating with silicone compounds is the selection of solvents in which the silicone oil is placed. Silicone oils are insoluble in mineral oil, water, most protic solvents and many other solvents. Most are soluble in mineral spirits which is volatile and limits the ability to formulate personal care products. Many attempts have been made to formulate silicone products which are useful in a variety of solvents.

Many attempts have been made to overcome these problems and get a truly substantive product, which deposits efficiently. One approach has been to use hydrosilation technology to make alkoxylated silicone polymers, used as raw materials in this invention. These materials do not have the substantivity desired to make them suitable for use as antistats, softeners and or soil release agents. Hydrosilation technology is known to those skilled in the art and is outlined in U.S. Pat. No. 4,083,856. These materials, prepared by the hydrosilation of a vinyl alkoxylated alcohol and a silanic hydrogen containing polymer, by virtue of their alkoxylation, exhibit a high cloud point classically seen in nonionics, which is a point were at some elevated temperature, the silicone polymer comes out of solution and becomes more substantive to the hydrophobic substrate. This approach allows for better efficiencies but does little if anything for long term substantivity.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is an ether linkage and a new hydroxyl group. While a definite improvement over earlier compounds the efficiency and durability of these compounds are not enough to allow for cost effective incorporation of these materials in detergent formulations.

U.S. Pat. No. 4,960,845 to O'Lenick issued October 1990 discloses sulfated silicone polymers which are high foaming surfactants.

U.S. Pat. No. 4,973,643 to O'Lenick issued November 1990 discloses ether amine compounds useful as raw materials in the preparation of the compounds of the present invention.

U.S. Pat. No. 3,801,572 to Berger issued April 1974 discloses amino silicones suitable as raw materials in the present invention.

U.S. Pat. No. 4,785,067 to Brumbill issued in 1988, discloses a partially neutralized, partially free amine, carboxylic acid salt for use as a protective coating and rust preventative.

THE INVENTION

Object of the Invention

It is the object of the present invention to provide a process utilizing a series of novel fatty carboxylic salts for treating hair and skin which comprises contacting the hair or skin with an effective conditioning amount of the novel compounds. The object of the treatment is to provide a nonirritating, non toxic, conditioning and softening to the substrate.

The properties of the compounds of the present invention make them useful in creams and lotions, mascaras, lipsticks and lip products, hair conditioners, hair styling products, eyeliners, shampoos and mousses.

Summary of the Invention

The present invention relates to a process for treating hair and skin with an effective conditioning amount of a novel fatty carboxylic acid salt of an amino silicone polymer. The polymers by virtue of the fact that they are fatty carboxylic salts deposit on substrate surfaces and form effective surface modifying finishes. The compounds of the present invention are substantive to not only to hair and skin but also to cellulosics, synthetic fibers, metal surfaces and plastic polymers.

The compounds of this invention conform to the following formula;

$$CH_3-\underset{\underset{CH_3}{|}}{\overset{\overset{CH_3}{|}}{Si}}-\left[O-\underset{\underset{R^1}{|}}{\overset{\overset{CH_3}{|}}{Si}}\right]_a-\left[O-\underset{\underset{R^2}{|}}{\overset{\overset{CH_3}{|}}{Si}}\right]_b-O-\underset{\underset{CH_3}{|}}{\overset{\overset{CH_3}{|}}{Si}}-CH_3 \quad Q[R^3]$$

a is an integer from 1 to 200;
b is an integer from 1 to 50;
$R^1$ is selected from —$CH_3$ or phenyl;
$R^2$ is selected from;

$$-(CH_2)_3-(OCH_2CH_2)_x-(OCH_2CH(CH_3))_y-(OCH_2CH_2)_z-\overset{\oplus}{NH_3};$$

or $$-(CH_2)_3-(CH_2)_v-\overset{\oplus}{N(H)_2}-[(CH_2)_3-\overset{\oplus}{N(H)_2}]_m-H;$$

x, y and z are integers ranging independently from 0 to 20, with the proviso that x+y+z is greater than 0;
v is an integer ranging from 0 to 5;
m is an integer from 1 to 10.
$R^3$ is the anion of a fatty carboxylic acid and conforms to the following structure;

$$\overset{\ominus}{O}-C(O)-R^4$$

$R^4$ is alkyl having from 5 to 45 carbon atoms or mixtures thereof;
Q is an integer needed for charge balance and is equal to the number of nitrogen atoms present in the R2 group.

The products of the present invention are prepared by neutralization of a the above specified silicone amines with a least an equivalent of a fatty carboxylic acid. This means that for each nitrogen atom present in the silicone pendant group there will be present at least one carboxylic acid anion. If less than a full equivalent of fatty acid is used in the preparation of the compounds of the present invention, the low level of irritation will not be acheived.

The salts of the primary amines have the amino group present at the terminal part of the pendant group and conform to the following structure;

$$-\overset{\oplus}{NH_3} \quad \overset{\ominus}{O}-C(O)-R \quad Q = 1$$

In the case were there is a diamine there will be a need for two equivalents of carboxylic acid to neutralize the amines.

$$-\overset{\oplus}{N(H_2)}-(CH_2)_2-\overset{\oplus}{NH_3} \quad \overset{\ominus}{O}-C(O)-R \quad Q = 2$$

$$\overset{\ominus}{O}-C(O)-R$$

It is clear therefore that the value of Q will equal the number of amine groups present in the silicone compound.

PREFERRED EMBODIMENT

In a preferred embodiment the number of carbon atoms in the fatty carboxylic acid ranges from 12 to 22. This results in a waxy paste which liquefies under pressure, and is excellent as a hair and skin conditioner and softener.

In another preferred embodiment the amines used for the neutralization are ether amines disclosed in U.S. Pat. No. 4,973,643 to O'Lenick. These amines are items of commerce marketed under the Silube trade name and available from Siltech Inc. Norcross Ga.

In another embodiment the molar ratio of amine to acid is between 1.0:1 to 1.5:1.0. The excess of acid results in a pH of about 5, which is close to the pH of skin and therefore is the desired pH for skin care products.

In still another preferred embodiment the compounds of the present invention are applied in an effective conditioning concentration to hair or skin. The compounds can be applied either in a shampoo or in a conditioning product. The effective conditioning concentration ranges from 0.001 to 25%, but the preferable concentration ranges from 0.1 to 5%.

RAW MATERIAL EXAMPLES

Fatty Acids

Fatty acids which are suitable for the preparation of compounds of the present invention include the following fatty acids and mixtures thereof. The compounds conform to the following structure;

| | R—C(O)—OH | |
|---|---|---|
| Name | R | Double Bonds |
| Caproic | $C_5H_{12}$ | 0 |
| Caprylic | $C_7H_{16}$ | 0 |
| Capric | $C_9H_{20}$ | 0 |
| Lauric | $C_{11}H_{24}$ | 0 |
| Myristic | $C_{13}H_{28}$ | 0 |
| Palmitic | $C_{15}H_{32}$ | 0 |
| Stearic | $C_{17}H_{36}$ | 0 |
| Arachic | $C_{19}H_{40}$ | 0 |

-continued

| | R—C(O)—OH | |
|---|---|---|
| Name | R | Double Bonds |
| Hydroxy Stearic | $C_{17}H_{36}O$ | 0 |
| Behenic | $C_{21}H_{44}$ | 0 |
| Lignoceric | $C_{24}H_{48}$ | 0 |
| Oleic | $C_{17}H_{34}$ | 1 |
| Erucic | $C_{21}H_{42}$ | 1 |
| Linoleic | $C_{17}H_{32}$ | 2 |
| Linolenic | $C_{17}H_{30}$ | 3 |
| Tetracosenic | $C_{24}H_{40}$ | 5 |
| TM | | |
| Unicid 700 | $C_{46}H_{92}$ | 0 |

Unicid TM is a trademark of Petrolite Specialty Polymers Group, Tulsa Okla.

Silicone Amines

The raw materials useful in the preparation of the compounds of the present invention can be divided into three classes depending upon the R2 group. All compounds have the following generic structure;

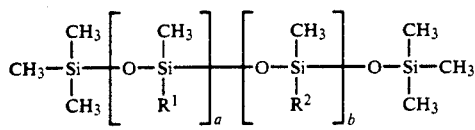

Class 1
$R^2$ is $-(CH_2)_3-(OCH_2CH_2)_x-(OCH_2CH(CH_3))_y-(OCH_2CH_2)_z-NH_2;$

| Example | $R^1$ | a | b | x | y | z |
|---|---|---|---|---|---|---|
| 1 | Methyl | 46 | 1 | 1 | 0 | 0 |
| 2 | Methyl | 150 | 4 | 5 | 5 | 5 |
| 3 | Methyl | 100 | 2 | 0 | 10 | 5 |
| 4 | Phenyl | 200 | 10 | 1 | 0 | 0 |
| 5 | Methyl | 20 | 20 | 0 | 1 | 0 |
| 6 | Ethyl | 50 | 1 | 20 | 20 | 20 |

Class 2
$R^2$ is $-(CH_2)_3-(CH_2)_w-N(H)-[(CH_2)_3-N(H)]_m-H;$

| Example | $R^1$ | a | b | w | m |
|---|---|---|---|---|---|
| 7 | Methyl | 100 | 4 | 0 | 1 |
| 8 | Methyl | 50 | 5 | 1 | 1 |
| 9 | Phenyl | 75 | 1 | 0 | 2 |
| 10 | Methyl | 175 | 10 | 0 | 1 |
| 11 | Methyl | 125 | 1 | 0 | 1 |
| 12 | Methyl | 200 | 10 | 4 | 1 |
| 13 | Phenyl | 50 | 1 | 5 | 1 |
| 14 | Methyl | 50 | 10 | 0 | 5 |

NEUTRALIZATION REACTIONS

General Procedure

The compounds of the present invention are prepared by the neutralization of the silicone amine by an equivalent amount of the fatty acid specified. The amine and fatty acid are added together and heated generally to between 100° and 140° C. until a clear homogeneous liquid is obtained. The reaction mass is then cooled to provide the desired product which is used without subsequent purification.

EXAMPLE 15

To a suitable mixing vessel with agitation and nitrogen sparge is added 282.0 grams of Behenic acid, and 3,566.0 grams of Silicone amine Example 1. The reaction mass is heated to 120° C. under agitation with a small amount of nitrogen being bubbled through the reaction mixture. The reaction mass clears and is allowed to cool. The product is used without additional purification.

EXAMPLE 16-28

Example 15 is repeated only this time substituting the specified amount of the specified amine for the silicone amine example 1 and the specified amount of the specified fatty acid for the behenic acid used in example 15.

| | Silicone Amine | | Fatty Acid | |
|---|---|---|---|---|
| Example | Example # | /Grams | Type | Grams |
| 16 | 1 | 3,566.0 | Caproic | 116.0 |
| 17 | 2 | 3,667.0 | Caprylic | 144.0 |
| 18 | 3 | 4,708.0 | Capric | 172.0 |
| 19 | 4 | 2,797.0 | Lauric | 200.0 |
| 20 | 5 | 200.0 | Myristic | 228.0 |
| 21 | 6 | 9,800.0 | Palmitic | 256.0 |
| 22 | 7 | 1,091.8 | Linoleic | 280.0 |
| 23 | 8 | 5,813.0 | Linolenic | 278.0 |
| 24 | 9 | 1,412.0 | Tetracosenic | 358.0 |
| 25 | 10 | 9,513.0 | Unicid 700 | 701.0 |
| 26 | 11 | 1,500.0 | Palmitic | 256.0 |
| 27 | 12 | 3,901.0 | Stearic | 284.0 |
| 28 | 13 | 974.0 | Arachic | 312.0 |

Applications Evaluation

Example 15 was subjected to battery of toxicity studies. The tests were conducted using the 100% active material. The results were as follows;

| Test | Result |
|---|---|
| Eye Irritation | Non-irritating |
| Skin Irritation | Non-irritating |
| Oral Toxicity | Non-toxic |
| Comedogenicity | Non-comedogenic |

Shampoo Formulation

The compounds of the present invention were also added to a simple shampoo formulation to show the potential for conditioning.

| | Control | A | B |
|---|---|---|---|
| Sodium Laureth Sulfate (30% Active) | 50.0 | 50.0 | 50.0 |
| Cocamide DEA | 3.0 | 3.0 | 3.0 |
| Sodium Chloride | 2.0 | 2.0 | 2.0 |
| Cocamidopropyl betaine | 2.0 | — | — |

-continued

|  | Control | A | B |
|---|---|---|---|
| (35% Active) | | | |
| Example # 21 | — | 0.5 | — |
| Example # 15 | — | — | 0.5 |
| Water | Quantity Sufficient to 100% | | |
| Total | 100.0 | 100.0 | 100.0 |

The above formulations were evaluated for softening properties and rated on a scale of 1-5. 5 being harshest.

| Softness Ratings | Rating |
|---|---|
| Control Formulation | 5 |
| Formulation A | 2 |
| Formulation B | 1 |

As the data clearly shows the compounds of the present invention are good conditioners and softeners when applied to the hair.

What is claimed;

1. A process for conditioning hair which comprises contacting the hair with an effective conditioning amount of a silicone compound which conforms to the following structure;

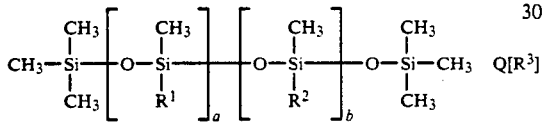

a is an integer from 1 to 200;
b is an integer from 1 to 50;
$R^1$ is $CH_3$;
n is an integer from 0 to 10;
$R^2$ is selected from the group consisting of;

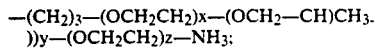

and

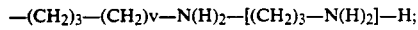

v is an integer ranging from 0 to 5;
x, y and z are integers independently ranging 0 to 20, with the proviso that x+y+x is greater than zero;
m is an integer from 10 to 10;
$R^3$ is the anion of a fatty carboxylic acid and conforms to the following structure;

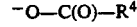

$R^4$ is alkyl having from 5 to 45 carbon atoms or mixtures thereof;
Q is an integer needed for charge balance and is equal to the number of nitrogen atoms present in the $R^2$ group
wherein said effective conditioning concentration ranges from 0.001 to 25%.

2. A process of claim 1 wherein
$R^2$ is —$(CH_2)_3$—$(OCH_2CH_2)x$—$(OCH_2$—$CH)CH_3$-))y—$(OCH_2CH_2)z$—$NH_3$;
x, y and z are integers independently ranging 0 to 20, with the proviso that x+y+z is greater than zero.

3. A process of claim 1 wherein $R^2$ is
—$(CH_2)_3$—$(CH_2)v$—$N(H)_2$—$[(CH_2)_3$—$N(H)_2$-]m—H;

m is an integer ranging from 1 to 5;
v is an integer ranging from 0 to 5.

4. A process of claim 3 wherein v is 0; m is 1.

5. A process of claim 2 wherein x is an integer from 1 to 10; y is 0; z is 0.

6. A process of claim 2 wherein the effective conditioning concentration ranges from 0.001 to 25%.

7. A process of claim 2 wherein the effective conditioning concentration ranges from 0.1 to 5%.

8. A process of claim 3 wherein the effective conditioning concentration ranges from 0.001 to 25%.

9. A process of claim 3 wherein the effective conditioning concentration ranges from 0.1 to 5%.

10. A process for conditioning skin which comprises contacting the skin with an effective conditioning amount of a silicone compound which conforms to the following structure:

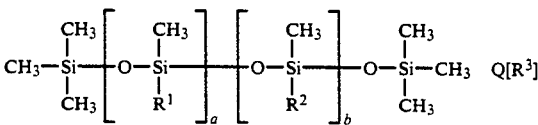

a is an integer from 1 to 200;
b is an integer from 1 to 50;
$R^1$ is $CH_3$;
n is an integer from 0 to 10;
$R^2$ is selected from the group consisting of;

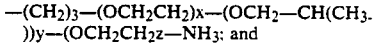

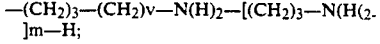

v is an integer ranging from 0 to 5;
x, y and z are integers independently ranging 0 to 20, with the proviso that x+y+z is greater than zero;
m is an integer from 1 to 10;
$R^3$ is the anion of a fatty carboxylic acid and conforms to the following structure:

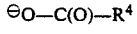

$R^4$ is alkyl having from 5 to 45 carbon atoms or mixtures thereof;
Q is an integer needed for charge balance and is equal to the number of nitrogen atoms present in the $R^2$ group.

11. A process for conditioning skin which comprises contacting the skin with an effective conditioning amount of a silicone compound which conforms to the following structure;

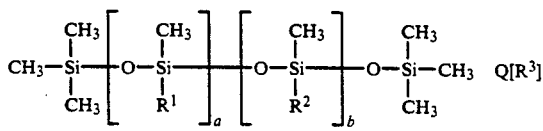

a is an integer from 1 to 200;
b is an integer from 1 to 50;
$R^1$ is $CH_3$;
n is an integer from 0 to 10;

$R^2$ is selected from the group consisting of:

—(CH$_2$)$_3$—(OCH$_2$CH$_2$)x—(OCH$_2$—CH(CH$_3$))y—(OCH$_2$CH$_2$)z—NH$_3$; and —(CH$_2$)$_3$—(CH$_2$)v—N(H)$_2$—[(CH$_2$)$_3$—N(H)$_2$]m—H;

v is an integer ranging from 0 to 5;

x, y and z are integers independently ranging 0 to 20, with the proviso that x+y+z is greater than zero;

m is an integer from 1 to 10;

$R^3$ is the anion of a fatty carboxylic acid and conforms to the following structure;

$^-$O—C(O)—R$^4$ $R^4$ is alkyl having from 5 to 45 carbon atoms or mixtures thereof;

Q is an integer needed for charge balance and is equal to the number of nitrogen atoms present in the $R^2$ group wherein said effective conditioning concentration ranges from 0.001 to 25%.

12. A process of claim 10 wherein $R^2$ is

—(CH$_2$)$_3$—(CH$_2$)v—N(H)$_2$—[(CH$_2$)$_3$—N(H)$_2$]m—H;

m is an integer ranging from 1 to 5;

v is an integer ranging from 0 to 5.

13. A process of claim 12 wherein v is 0; m is 1.

14. A process of claim 11 wherein x is an integer from 1 to 10; y is 0; z is 0.

15. A process of claim 12 wherein the effective conditioning concentration ranges from 0.001 to 25%.

16. A process of claim 12 wherein the effective conditioning concentration ranges from 0.1 to 5%.

17. A process of claim 11 wherein the effective conditioning concentration ranges from 0.001 to 25%.

18. A process of claim 11 wherein the effective conditioning concentration ranges from 0.1 to 5%.

* * * * *